US005554502A

United States Patent [19]
Mitsuhashi et al.

[11] Patent Number: 5,554,502
[45] Date of Patent: Sep. 10, 1996

[54] PROCESS FOR DETERMINING NUCLEASE ACTIVITY

[75] Inventors: Masato Mitsuhashi; Mieko Ogura, both of Irvine, Calif.

[73] Assignees: Hitachi Chemical Co. Ltd., Japan; Hitachi Chemical Research Center Inc., Irvine, Calif.

[21] Appl. No.: 147,936

[22] Filed: Nov. 5, 1993

Related U.S. Application Data

[63] Continuation-in-part of Ser. No. 125,361, Sep. 22, 1993, abandoned.

[51] Int. Cl.[6] .............................. C12Q 1/00; C12Q 1/68; G01N 21/76; C12N 15/00
[52] U.S. Cl. ............................ 435/6; 435/4; 435/74; 436/172; 436/800; 935/76; 935/77
[58] Field of Search ....................... 435/968, 4, 6, 435/7.4; 436/172, 800; 935/76, 77, 82

[56] References Cited

PUBLICATIONS

Rye et al. Analytical biochemistry 208 pp. 144–150 (1993).

Kurnick, Methods of Biochemical Analysis vol. IX, (1962) Intersciences Publishers John Wiley & Sons.

Analytical Biochemistry, vol. 208, issued Jan. 1993, Rye et al., "Fluorometric Assay Using Dimeric Dyes for Double– and Single–Stranded DNA and RNA with Picogram Sensitivity", pp. 144–150.

*Primary Examiner*—Carolyn Paden
*Attorney, Agent, or Firm*—Knobbe Martens Olson & Bear

[57] ABSTRACT

The present invention relates to analyzing a test sample for the presence or absence of nuclease activity, and for quantifying the amount of nuclease activity. In one aspect of the invention, a kit is provided which allows the rapid and efficient quantification of nuclease activity in a sample having an unknown nuclease activity. In another aspect of the invention, a method for determining the presence or absence of nuclease activity, and for quantifying nuclease activity is disclosed.

24 Claims, 5 Drawing Sheets

PROCESS FOR DETERMINING NUCLEASE ACTIVITY

RELATED APPLICATION

This application is a Continuation-In-Part of application Ser. No. 08/125,361, filed Sep. 22, 1993, now abandoned the disclosure of which is hereby incorporated by reference.

BACKGROUND

1. Field of the Invention

The present invention relates to a method and kit for determining the presence and quantity of nuclease activity in a sample having an unknown nuclease activity.

2. Background of the Art

The contamination of laboratory equipment and solutions by nucleases is highly problematic in experiments involving nucleic acids, because these contaminating enzymes can break down the nucleic acids essential to the experiment. To avoid this problem, nuclease-free chemicals must be purchased from vendors, and equipment and solutions must be autoclaved or treated with DEPC before and during experimentation.

Contamination is a particular problem for large manufacturing facilities producing molecular biology-grade chemicals, because of quality control protocols. Further, monitoring for contamination by nucleases is needed during the purification and characterization of nucleases.

Assaying for contamination by nucleases is not now routinely carried out because the presently available methods for assaying are too time-consuming, or require expertise or materials not readily available. Of the several heretofore available methods, the most commonly used is monitoring the degradation of DNA and RNA by measuring the variation in optical density at 260 nanometers. This method, however, requires expensive quartz glass cuvettes, and is particularly time-consuming when analyzing a large number of samples. (Blackburn, et al., Journal of Biological Chemistry, Vol. 252, No. 16, (1977)).

Nuclease activity can also be determined by measuring the radioactive decay of $^{32}P$-labeled DNA or RNA. This technique requires multiple steps to separate intact DNA and RNA from digested nucleic acids, and entails the handling of radioactive materials.

Still another method of measuring nuclease activity is to electrophoretically separate digested DNA and RNA from undigested DNA and RNA, and stain the undigested DNA and RNA bands with ethidium bromide. (March and Gonzalez, Nucleic Acids Research, Vol. 18, No. 11, (1990)). This method takes considerable amounts of time and, thus, is not suitable for detection of nuclease activity in a large number of samples.

DNase activity has also been determined using an antibody capture bioassay. In this method, DNase in test samples is trapped in anti-DNase polyclonal antibody-coated microtiter plates. (Gibson, et al., Journal of Immunological Methods 155, 249 (1992)). The difficulty with this technique is that it requires antibodies with specificity against the particular nuclease of interest, and these antibodies have limited availability.

Thus, there remains a need for a method to determine the presence and quantity of nuclease activity in a sample having an unknown nuclease activity that is both cost-effective and capable of being performed in a reasonable period of time.

There are a variety of commercially-available, fluorescing, nucleic acid dyes. These include ethidium bromide, in addition to newer dyes made from the general groups of benzoxazolium-4-pyridinium, benzothiazolium-4-pyridinium, benzoxazolium-4-quinolinium, Yoyo-1, Toto-1, Toto-3.

The effects of ethidium bromide on nuclease activity have been documented in a number of previous experiments. In one study, ethidium bromide intercalation with DNA in chromatin increased the digestion rate by micrococcal nuclease. However, ethidium bromide intercalation with free DNA inhibits the digestion rate by micrococcal nuclease. In the former case, the micrococcal nuclease recognizes sites different from that of non-intercalated DNA in chromatin. (Jerzmanowski, et al., Biochimica et Biophysica Acta, 521:493–501, (1978)). Similarly, pre-treatment of DNA with ethidium bromide caused an alteration in the recognition sites by Exonuclease III on DNA which was combined with the anti-tumor drug cis-diamminedi-chloroplatinum (II). (Tullius & Littard, Proceedings of the National Academy of Science U.S.A., Vol. 72, pp. 3489–3492 (1982)).

In another experiment, ethidium bromide intercalation of DNA was found to decrease the activity of $S_1$ nuclease. (Alvi, Rizvi, and Hadi, Chemical Biological Interactions, Vol. 53, pp. 219–231 (1985)). Similarly, ethidium bromide intercalation of mitochondrial and plasmid pBR322 DNA inhibited the activity of various restriction endonucleases, but the inhibition varied depending on the restriction site. (Soslau and Pirollo, Biochemical and Biophysical Research Communications, Vol. 115, No. 2 (1983)). An endonuclease purified from chicken liver was found to have increased activity on heat-denatured DNA and on native DNA that was pre-treated with intercalating agents, including ethidium bromide. (Rizvi and Hadi, Indian Journal of Biochemistry and Biophysics, Vol. 19, pp. 394–398 (1982)).

As can be appreciated frown the above experiments, the effects of intercalating agents on nuclease activity, as represented by ethidium bromide, depends on the state of the DNA and the nuclease. The effects of the newer nucleic acid dyes on nuclease activity upon any of the various nucleic acid substrates was, heretofore, unknown.

SUMMARY OF THE INVENTION

We have discovered a process for the detection and quantification of nuclease activity in a test sample having an unknown quantity of nuclease activity. The method is efficient in terms of time and materials, and does not require either radioactive isotopes or antibodies. The method can be used on all known types of nucleases.

In one aspect, the present invention provides a method for the rapid and efficient detection and quantification of nuclease activity in a test sample having an unknown quantity of nuclease activity. The method includes the steps of 1) providing a plate having a plurality of wells, at least one of the wells being a control well and at least one additional well being a test well, wherein each of the wells contains a known quantity of polynucleotide and a dye having a partition coefficient greater than $10^6$, more preferably greater than $10^7$, with the polynucleotide, 2) adding a known quantity of nuclease to each control well and adding a test sample, with an unknown nuclease activity, to each test well, 3) detecting the fluorescence in the control and test wells by CytoFluor® 2300, or an equivalent device, and 4) comparing the detected fluorescence to each other.

The presence of nuclease activity in the test sample is determined by the decreasing fluorescence with time. Quantification of nuclease activity in the test sample can be determined by plotting the fluorescence of the test sample against a standard plot calculated from the control well fluorescence values. A detected amount of fluorescence in the test well greater than a detected amount of fluorescence in the control well indicates less nuclease activity in the test well. Similarly, a detected amount of fluorescence in the test well less than a detected amount of fluorescence in the control well indicates greater nuclease activity in the test well.

Another aspect of the present invention is a kit for the detection and quantification of nuclease activity in a sample having an unknown nuclease activity. The kit comprises a plate having: a plurality of wells, at least one of which is a control well and at least another of which is a test well. Each of the wells contains 1) a known quantity of polynucleotide, and 2) a polynucleotide dye having a partition coefficient greater than $10^6$, more preferably $10^7$, with the polynucleotide. In addition, the kit further comprises a nuclease in a container apart from the nucleotide.

In a parallel experiment, all three components, DNA, DNase and Yoyo-1, were mixed and incubated at room temperature for various lengths of time. The fluorescence intensity of Yoyo-1 was then measured as above (closed circles).

Figure 1:
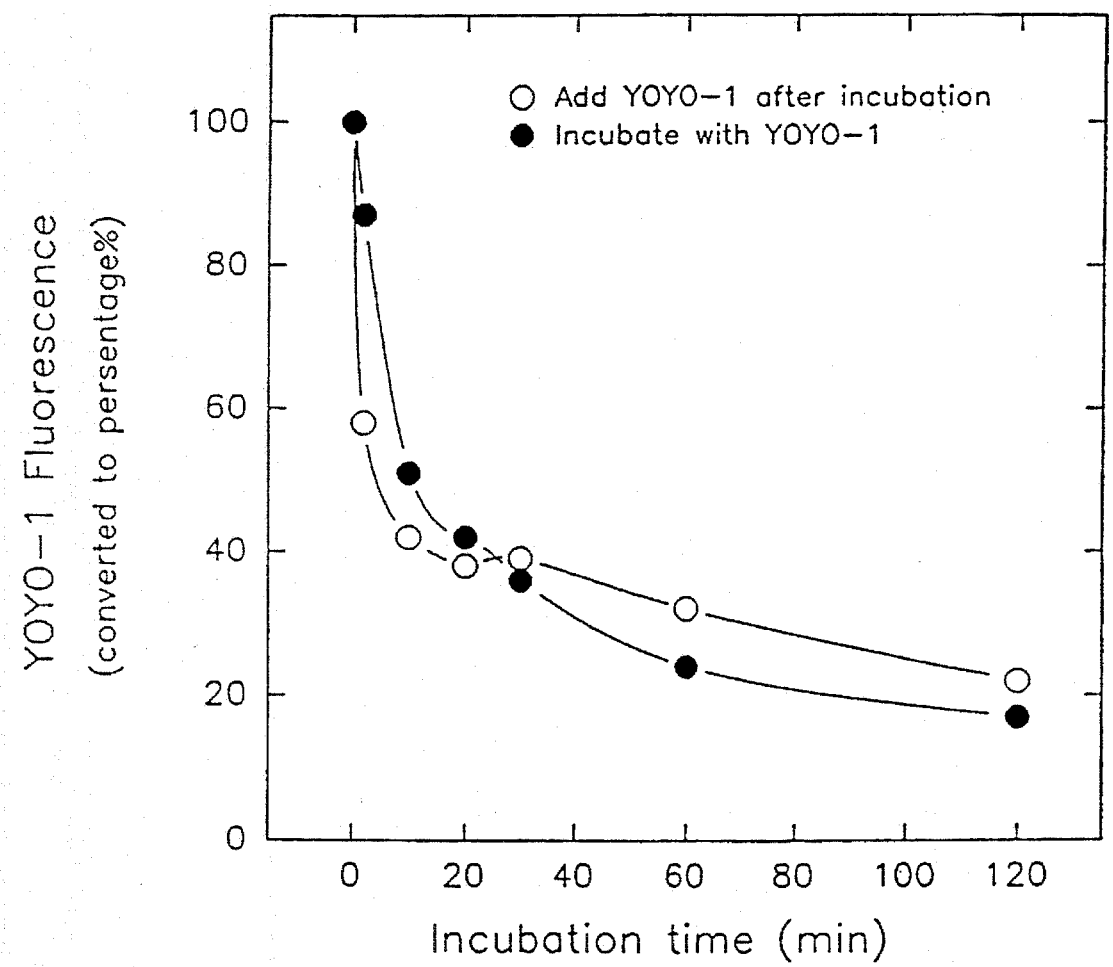
FIG. 1 is a line graph comparing the fluorescence of a suspended mixture of Yoyo-1, DNA and DNase in which the Yoyo-1 is added after incubation with DNase (open circles), with a suspended mixture of Yoyo-1, DNA and DNase in which the Yoyo-1 is added before incubation with DNase (closed circles). In this experiment, 0.5 micrograms of DNA and 10 units of DNase in a final volume of 50 microliters of TAE buffer (10 millimolar Tris-acetate, pH 7.6 containing 1 millimolar EDTA) were incubated at room temperature for various lengths of time in polypropylene 96 well microtiter plates. After incubation, Yoyo-1 in a final concentration of 1:1000 dilution in TAE buffer was added to each well. The fluorescence intensity was measured with a CytoFluor® 2300 fluorimeter (open circles), with excitation and emission wavelengths of 492 nanometers and 510 nanometers, respectively.
Figure 2:
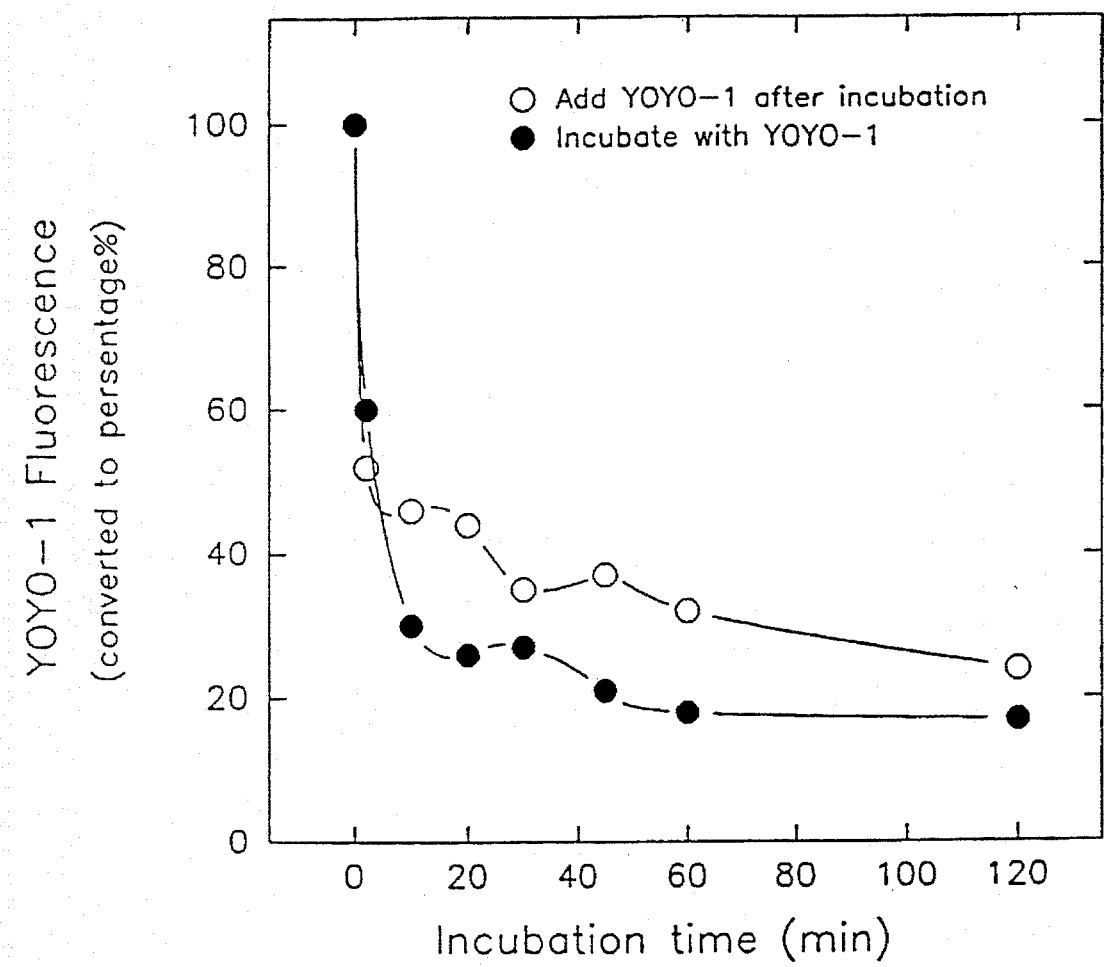

FIG. 2 is a line graph comparing the fluorescence of a suspended mixture of Yoyo-1, RNA and RNase in which the Yoyo-1 is added after incubation with RNase (open circles), with a suspended mixture of Yoyo-1, RNA and RNase in which the Yoyo-1 is added before incubation with DNase (closed circles). The experimental parameters were identical to those used to produce FIG. 1, except that 0.3 micrograms of RNA and 1 unit of RNase when used instead of DNA and DNase.

Figure 3A:
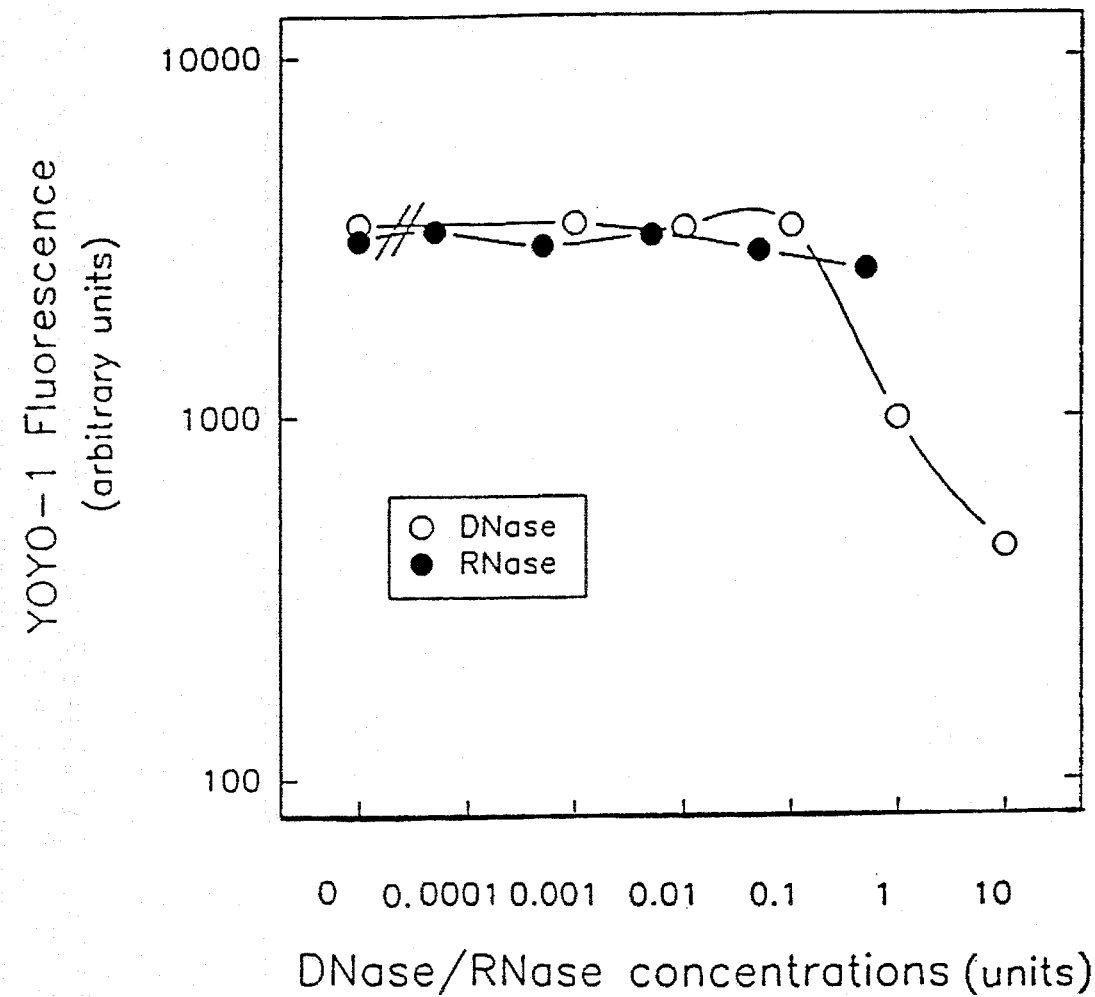
Figure 3B:
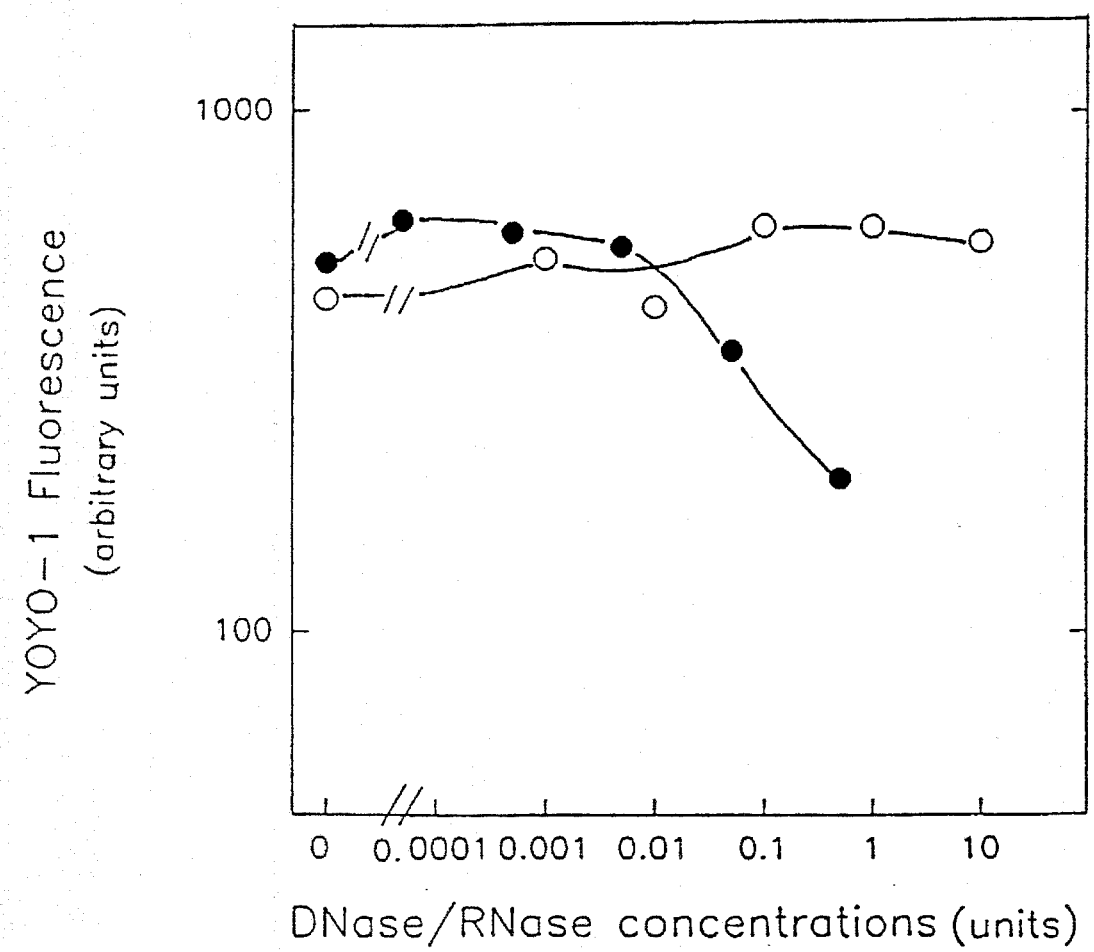

FIGS. 3A and 3B are line graphs showing the effects of RNase and DNase, respectively, on dried nucleic acid-Yoyo-1 complexes which have been resuspended. In these experiments, 125 ng of DNA (closed circles) or 500 ng of RNA (open circles), and 1:200 dilution of Yoyo-1 in a final volume of 10 microliters of TAE buffer was applied to each well of polypropylene 96 well microtiter plates and stored at room temperature until dry. Various concentrations of DNase (closed circles) or RNase (open circles) were applied to each well and incubated at room temperature for 60 minutes. The fluorescence intensity of individual wells were measured with a CytoFluor® 2300 fluorimeter, as described in connection with FIG. 1.

Figure 4:
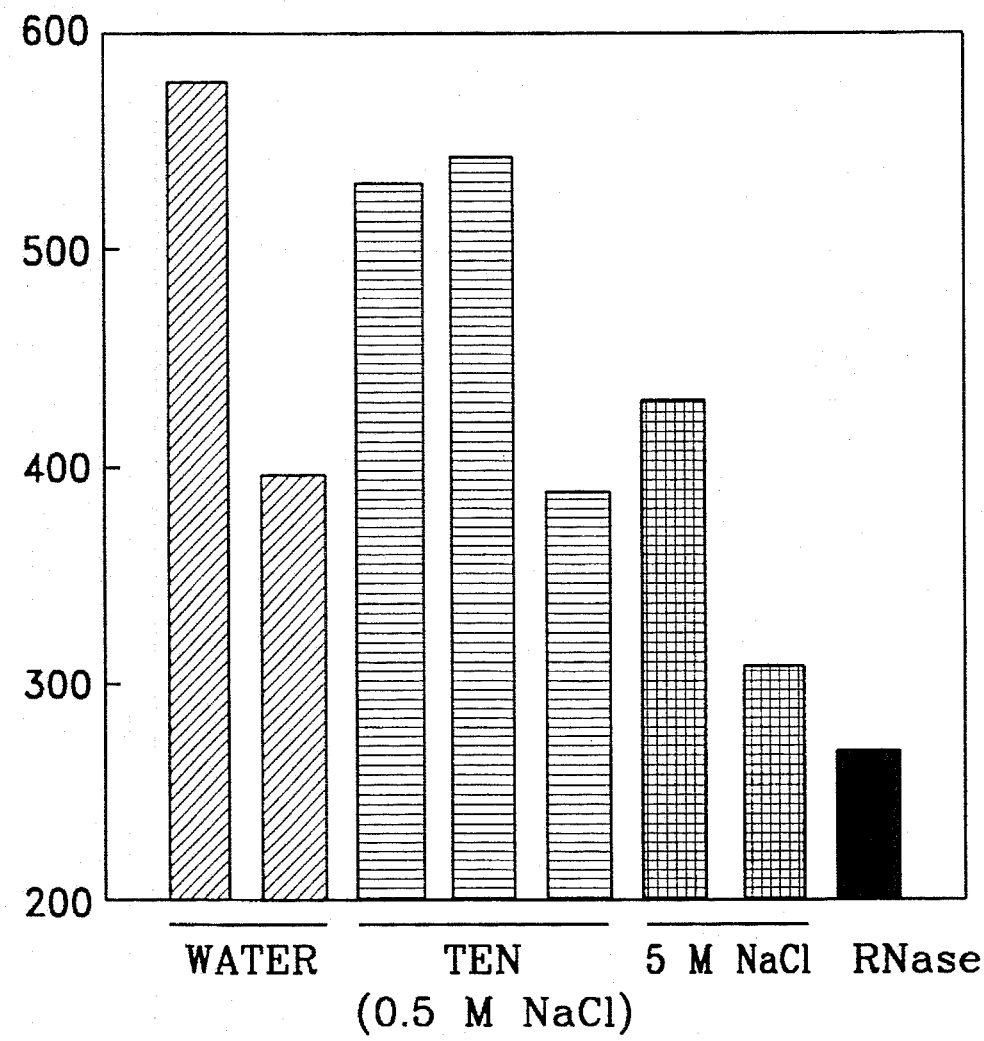

FIG. 4 is a bar graph showing the results of contamination tests of various buffers. Forty-five microliters of non-treated water, tris EDTA in 0.5 molar NaCl (TEN) and 5 molar NaCl were applied to each well of polypropylene 96-well plates. In addition, DEPC water was used as a negative control and DEPC water with 1 unit of RNase was used as a positive control. Five microliters of Yoyo-1 (1:100 dilution in TAE buffer) was added to each well to achieve a final 1:1000 dilution of Yoyo-1. The fluorescence intensity was measured with a CytoFluor® 2300 fluorimeter.

DETAILED DESCRIPTION OF THE PREFERRED EMBODIMENTS

The present invention relates to a series of discoveries we made concerning the influence of Yoyo-1 on nuclease activity. As discussed above, older-type intercalating dyes, such as ethidium bromide, have a variety of effects on nuclease activity depending on the nuclease and the state of the DNA. We conducted a series of experiments on the effects of Yoyo-1, a newer benzoxazolium-4-quinolinium dye, on nuclease activity. While it has been known that Yoyo-1 could be used to detect DNA and RNA in a quantitative manner, it was unknown whether intact nucleic acid-Yoyo-1 complex fluorescence was different than digested nucleic acid-Yoyo-1 complex fluorescence. It was also unknown whether nucleases could digest DNA or RNA-Yoyo-1 complexes or if such digestion occurred in a quantitative manner.

The present invention provides a significant improvement in the detection and quantification of nuclease activity. In one preferred embodiment, the present invention comprises a kit containing a microliter plate, such as a polypropylene plate, upon which are a plurality of wells. The number of wells can vary with the intended use, but there must be at least one test well and one control well on each plate. If the intended use is the detection of nuclease activity only, then a minimum of one test and one control well may be present. If the intended use is the quantification of nuclease activity, then there must be at least one test well and at least two or more control wells. As will be appreciated by one of skill in the art, increasing the number of control wells which have different known quantities of nuclease increases the precision with which one can quantify nuclease activity in the unknown.

Dried onto each well is a known quantity of polynucleotide and a dye. It is anticipated that the polynucleotide chosen could be either DNA or RNA, in any of the following forms: single-stranded, double-stranded or circular single- or double-stranded, with either blocked or unblocked 3' or 5' ends, synthetic oligonucleotides with or without chemical modifications, a hybrid of any of the foregoing or, a mixture of two or more such forms. RNA was extracted as follows; Jurkat human T-cell were obtained from America Type Culture Collection (Bethesda, Md.) and maintained in a RPMI-1640 media containing 10% fetal calf serum and appropriate antibiotics. The cells were washed with phosphate buffered saline three times and then suspended in a lysis buffer (10 mM Tris, pH 7.6, containing 1 mM EDTA, 0.5M NaCl, 0.1% NP-40, and 500 units/ml RNasin®. Cell lysates were immediately vortexed and placed on ice for 2 minutes. After centrifugation in a microfuge, supernatants were extracted with phenol/chloroform/isoamyl alcohol (25:24:1) once, chloroform once, and precipitated in ethanol at −20° overnight. After the pellets were washed with 70% ethanol once, the pellets were dried under Speed Vac (Savant, Farmingdale, N.Y.). Dried RNA preparation was then suspended in DEPC-treated water, and concentrations were determined at $OD_{260}$.

The dye used should have a partition coefficient of at least $1 \times 10^6$, and more preferably at least $10^7$, in a 10% ethanol/water solution (i.e., $10^6$ or $10^7$ times more dye bound to the DNA than dye in the ethanol/water solution). These dyes intercalate with polynucleotide efficiently. Preferred examples of such dyes include Yoyo-1, having a partition coefficient of $6.0 \times 10^8$, Toto-1, having a partition coefficient of $1.1 \times 10^9$, and Toto-3, having a partition coefficient of $2.5 \times 10^8$. A variety of other suitable dyes are known to those of skill in the art. Yoyo-1 iodide and Toto-1 iodide are available from Molecular Probes, Eugene, Oreg. Preparation of the dyes is preformed by suspension in 40 mM Tris-acetate, pH 8.2, containing 1 mM (TAE buffer) at various concentrations. Additional dyes suitable for use in connection with the present invention are shown in Table 1.

TABLE 1

Characteristics of Various Thiazolium and Axazolium Nucleic Acid Stains

| Catalog Number (Molecular Probes) | Dye* | EX max/ EM max (nm)** | $\epsilon \times 10^{-3}$†/ (QY)** | Kp‡ |
|---|---|---|---|---|
| None | Thiazole orange | 509/525 | 54/(0.2) | $4.8 \times 10^6$ |
| P-3581 | PO-PRO-1 | 435/455 | 50/(0.39) | $2.0 \times 10^6$ |
| B-3583 | BO-PRO-1 | 462/481 | 58/(0.16) | $3.2 \times 10^6$ |
| Y-3603 | YO-PRO-1 | 491/509 | 52/(0.44) | $8.2 \times 10^6$ |
| T-3602 | TO-PRO-1 | 515/531 | 62/(0.25) | $2.0 \times 10^7$ |
| P-3585 | PO-PRO-3 | 539/567 | nd/(nd) | nd |
| B-3587 | BO-PRO-3 | 575/599 | nd/(nd) | $4.8 \times 10^6$ |
| Y-3607 | YO-PRO-3 | 612/631 | 100/(0.16) | $3.3 \times 10^6$ |
| T-3605 | TO-PRO-3 | 642/661 | 102/(0.11) | $6.2 \times 10^6$ |
| P-3580 | POPO-1 | 434/456 | nd/(nd) | nd |
| B-3582 | BOBO-1 | 462/481 | nd/(nd) | nd |
| Y-3601 | YOYO-1 | 491/509 | 84/(0.52) | $6.0 \times 10^8$ |
| T-3600 | TOTO-1 | 514/533 | 112/(0.34) | $1.1 \times 10^9$ |
| P-3584 | POPO-3 | 534/570 | 146/(0.46) | nd |
| B-3586 | BOBO-3 | 570/602 | 148/(0.39) | nd |
| Y-3606 | YOYO-3 | 612/631 | 167/(0.15) | $1.5 \times 10^8$ |
| T-3604 | TOTO-3 | 642/660 | 154/(0.06) | $2.5 \times 10^8$ |
| E-1169 | EthD-1 | 528/617 | 7.4/(0.08) | $5.0 \times 10^8$ |
| E-3599 | EthD-2 | 535/626 | nd/(nd) | $1.0 \times 10^9$ |

*All the PO stains are benzoxazolium-4-pyridinium dyes.
BO stains are benzothiazolim-4-pyridinium dyes.
YO stains are benzoxazolium-4-quinolinium dyes.
TO stains are benzothiazolium-4-quinolinium dyes.
**Quantum yields (QY) and spectral data are of the dye bound to excess calf thymus DNA (50 bp/dye).
† $cm^{-1}M^{-1}$
‡ DNA partition coefficient in a 10% ethanol/water solution
nd Not determined Table 1 lists various different dyes and their corresponding DNA partition coefficients. These coefficients are related to the amount of dye that remains in a DNA sample after saturation in a 10% ethanol/water solution. A dye having a coefficient of at least $1 \times 10^7$ (i.e. $1 \times 10^7$ times more dye bound to the DNA sample than in the ethanol/water solution) is preferred in this invention as these dyes intercalate with the DNA very efficiently. However, dyes having a coefficient as low as $10^6$ are suitable in many applications.

One preferred dye is TOTO-3 because it can be excited with a 630 nm laser which is available to those in the art. In addition, TOTO-3 emits photons, upon excitation, at 660 nm, which is different enough from the excitation wavelength to provide easy detection.

Another preferred photometric dye for staining polynucleotides is Yoyo-1, a fluorescent complex that intercalates and reacts with double-stranded nucleic acid sequences. Specifically, Yoyo-1 is an oxazole yellow homodimer.

When complexed with a double-stranded piece of DNA, a multichromophore label is formed that can be subjected to a fluorescence assay. Glazer, A. N. et al. *Nature*, 359:859–861 (1992). Yoyo-1 has an excitation wavelength of 485 nm. After excitation Yoyo-1 emits photons at 530 nm. Both of these wavelengths are in the visible light spectrum.

Other dyes are also contemplated, such as, Toto-1, thiazole orange, or those dyes within the group of benzoxazolium-4-pyridinium, benzothiazolium-4-pyridinium, benzoxazolium-4-quinolinium, and benzothiazolium-4-quinolinium florescent dyes that show advantageous spectrographic sensitivity for the analysis of nucleic acid sequences. These dyes have excitation wavelengths from the low 400 nm range and emission wavelengths up to the high 600 nm range when bound to a nucleic acid sequence. Such dyes are commercially available from companies such as Molecular Probes, Inc.

The nuclease chosen should be one either known to be capable of digesting the polynucleotide in the wells or one suspected of contaminating a sample. Nucleases used for one preferred embodiment included RNase free DNase (1000 U/ml, Promega, Madison, Wis.) and RNase Cocktail (10,000 U/ml, Stratagene, La Jolla, Calif.).

The kit further comprises the chosen nuclease in a container separated from the dried polynucleotide-dye complex. The container may be totally detached from the plate, such as in separate vials. In another embodiment, the nuclease could be enclosed in a chamber which is attached to the well but separated from the dried polynucleotide-dye complex by a perforatable wall. One example of such an arrangement would be a chamber below each well containing nuclease such that once the chamber is squeezed, the perforatable wall would break combining the nuclease to the dried polynucleotide-dye complex.

The source of penicillin-streptomycin was Irvine Scientific (Irvine, Calif.). The source of the other chemicals used was Sigma (St. Louis, Mo.).

Fluorescence can be measured using any of a number of well-known fluorimeters. We used a CytoFluor® 236,0 Fluorescence Measurement System (Millipore, Bedford, Mass.) with excitation and emission wavelengths of 485 nm (bandwidth 20 nm) and 530 nm (bandwidth 2:5 nm) for Yoyo-1 iodide.

One preferred embodiment of the kit is constructed as follows; a 96 well polypropylene plate is autoclaved to remove contamination with unwanted nucleases. Fifty microliters of Yoyo-1 iodide solution and 0.3 micrograms of RNA are added to each well on the plate and allowed to dry. RNase Cocktail is provided in vials separated from the plate in the following concentrations: 10 U, 1 U, 0.1 U, 0.01 U, 0.001 U and 0.0001 U. One or more wells are designated as test wells. Another aspect of the present invention comprises a method for the rapid and efficient detection and quantification of nuclease activity in a test sample having an unknown quantity of nuclease activity. The method includes the steps of 1) providing a plate having a plurality of wells, at least one of the wells being a control well and at least one additional well being a test well, wherein each of the wells contains a known quantity of polynucleotide and a dye having a partition coefficient greater than $10^7$ with the polynucleotide, 2) adding a known quantity of nuclease to each control well and adding a test sample, with an unknown nuclease activity, to each test well, 3) detecting the fluorescence in the control and test wells, and 4) comparing the detected fluorescence to each other.

In one preferred embodiment, the kit described above is used. The nuclease is in vials apart from the plate and is added to multiple wells (for quantification of the unknown nuclease activity) such that each concentration of nuclease is added to at least one well, and preferably more than one well. At the same time, the unknown is added to at least one test well. Fluorescence is measured at the wavelengths described above, serially, and data recorded for between 5 and 60 minutes depending on the accuracy required. The method is carried out at room temperature or at 37° C.

Once the data is obtained, values recorded from multiple control wells having had the same concentration of nuclease can be averaged. Similarly, values from multiple test wells having the same unknown can be combined.

The presence of nuclease activity in the test sample is determined by the decreasing fluorescence with time. Quantification of nuclease activity in the test sample is determined by plotting the fluorescence of the test sample against a standard plot calculated from the control well fluorescence values. For example, fluorescence can be plotted on the y axis and time on the x axis. The data from the control wells will generate a series of standardizing line graphs, one for each concentration of nuclease used in the control wells.

The nuclease activity present in the unknown can be determined by co-plotting the data obtained from the test well(s). A detected amount of fluorescence in a test well greater than a detected amount of fluorescence in a control well indicates less nuclease activity in the test well. Similarly, a detected amount of fluorescence in a test well less than a detected amount of fluorescence in a control well indicates greater nuclease activity in the test well.

As will be appreciated by one with skill in the art, the method described above can be used to test multiple unknowns simultaneously. Further, once a standardized plots are obtained, they can be used to determine nuclease activity in multiple unknowns, within a same plate.

By this method, nuclease activity in a wide variety of unknowns can be determined. Further, potential nucleases can be rapidly characterized.

In one particularly preferred method, a 633 nm laser can be used to excite polynucleotides complexed with a dye, such as TOTO-3 having an excitation maximum near this wavelength. We have found that this laser can produce approximately 5–8 times more fluorescence than excitation by fluorescence spectrophotometer, even if the spectrophotometer was set for the excitation maximum for TOTO-3.

The following are specific experiments we performed using the methods of the present invention. These experiments are provided in order to exemplify certain preferred embodiments of the invention. As such, these experiments are not intended to limit the scope of the invention.

EXPERIMENT 1

Comparison of Fluorescence of Suspended DNA, DNase and Yoyo-1, when Adding Yoyo-1 Either Before and After Incubation with DNase Referring now to FIG. 1, 0.5 micrograms of DNA and 10 units of DNase in a final volume of 50 microliters of TAE buffer (10 millimolar Tris-acetate, pH 7.6 containing 1 millimolar EDTA) were incubated at room temperature for various lengths of time in polypropylene 96 well microtiter plates. After incubation, Yoyo-1 in a final concentration of 1:1000 dilution in TAE buffer was added to each well. The fluorescence intensity was measured with a CytoFluor® 2300 fluorimeter (open circles), with excitation and emission wavelengths of 492 nanometers and 510 nanometers, respectively.

In a parallel experiment, all three components, DNA, DNase and Yoyo-1, were mixed and incubated at room temperature for various lengths of time. The fluorescence intensity of Yoyo-1 was then measured as above (closed circles).

It can be seen in FIG. 1 that Yoyo-1 fluorescence decreases with incubation time as its complexed DNA is digested by DNase (closed circles). Similarly, Yoyo-1 fluorescence decreases with incubation time when Yoyo-1 is added after DNA and DNase are first incubated together without Yoyo-1 (open circles). Note that these two curves essentially superimpose. This suggests that 1) DNA-Yoyo-1 complex can be a target for DNase, and 2) DNase has approximately the same digestion kinetics for DNA-Yoyo-1 complex as for DNA that is not complexed with Yoyo-1.

EXPERIMENT 2

Comparison of Fluorescence of Suspended RNA, RNase and Yoyo-1, when Adding Yoyo-1 Either Before and After Incubation with RNase Referring now to FIG. 2, the parameters of Experiment 1 were repeated using 0.3 micrograms of RNA and 1 unit of RNase in place of DNA and DNase. The results of Experiment 2 indicate that Yoyo-1 fluorescence is essentially the same regardless whether the Yoyo-1 is added before the RNase or after the RNase and RNA have incubated for a period of time. Equivalent to Experiment 1, the results of Experiment 2 suggest that 1) RNA-Yoyo-1 complex can be a target for RNase, and 2) RNase has approximately the same digestion kinetics for RNA-Yoyo-1 complex as for DNA that is not complexed with Yoyo-1. Taken together, Experiment 1 and Experiment 2 imply that Yoyo-1 added to a suspension of polynucleotide does not affect nuclease activity when the nuclease is added subsequently and that nuclease digested polynucleotides are no longer a target for complexing with Yoyo-1.

EXPERIMENT 3

Effect on Fluorescence of Drying Nucleic Acid-Yoyo-1 Complex Before Resuspending and Treating with Nuclease It was previously unknown whether dried nucleic acids-Yoyo-1 complex could be digested by nuclease after resuspending in solution. This question was examined in Experiment 3. In these tests, 125 ng of DNA (closed circles) or 500 ng of RNA (open circles), and 1:200 dilution of Yoyo-1 in a final volume of 10 microliters of TAE buffer was applied to each well of polypropylene 96 well microtiter plates and stored at room temperature until dry. Various concentrations of DNase (closed circles) or RNase (open circles) in a final volume of 50 μl were applied to each well and incubated at room temperature for 60 minutes. The fluorescence intensity of individual wells were measured with a CytoFluor® 2300 fluorimeter, as described above in Experiment 1.

Referring now to FIG. 3, the results of Experiment 3 showed that when dried DNA and Yoyo-1 were resuspended in a solution containing DNase, a decrease in the fluorescence of Yoyo-1 occurred that is does dependent on the amount of DNase added (closed circles). A similar result was obtained using dried and resuspended RNA-Yoyo-1 complex (open circles).

This experiment demonstrated that 1) resuspended, dried polynucleotide-Yoyo-1 complex is a suitable substrate for nuclease, and 2) that the decrease in the fluorescence of polynucleotide-Yoyo-1 complex is dose dependent on the amount of nuclease added, such that the amount of nuclease activity can be determined quantitatively after resuspension of dried polynucleotide Yoyo-1 complex. Hence, interim drying of polynucleotide-Yoyo-1 complex does not appear to affect quantitative determination of nuclease activity, once the dried polynucleotide-Yoyo-1 complex is resuspended and used as a target for the nuclease.

EXPERIMENT 4

Test of Contamination by Nuclease of Various Buffers

We tested various commonly used buffers for contamination by nuclease. Referring now to FIG. 4, 45 microliters of buffers and control solutions were applied to the wells of polypropylene 96-well plates. DEPC water was applied to some wells (as a negative control, bar #1, numbering from left to right), non-treated water to some wells (bar #2), tris EDTA in 0.5 molar NaCl (TEN) to some wells (bars #3, 4, 5), 5 molar NaCl to some wells (bars #6 and 7), and DEPC water and 1 unit of RNase to other wells (as a positive control, bar #8, right-most bar). Five µl of Yoyo-1 diluted at 1:100 in TAE buffer was added to each well to make a final Yoyo-1 dilution of 1:1000. The fluorescence intensity was measured with a CytoFluor® 2300 fluorimeter.

As can be appreciated from FIG. 4, all samples tested had fluorescence intensities less than the negative control, bar #1, indicating some level of contamination. Bars #2, 5, 6 and 7 indicated significant contamination with nuclease but note that the amount of contamination varied widely. Hence, Experiment 4 shows the need to neutralize nuclease contamination in total or in the alternate, the need for a method to check quantitatively for contamination.

What is claimed is:

1. A kit for detection and quantification of nuclease activity in a sample having an unknown nuclease activity, comprising the following components:

a plate having a plurality of wells therein, at least one of said wells being a control well and at least one of said wells being a test well, each of said test and control wells containing a known quantity of a polynucleotide and a thiazolium or azolium dye having a partition coefficient greater than $10^7$ with said polynucleotide, wherein each of said test wells is for simultaneously containing a sample containing a nuclease to be quantified and polynucleotide-dye complexes formed from said polynucleotide and said dye; and a nuclease in a container apart from said polynucleotide, wherein each of said control wells is for simultaneously containing a known quantity of said nuclease and polynucleotide-dye complexes formed from said polynucleotide and said dye.

2. The kit of claim 1, wherein said polynucleotide and dye are dried onto said plate.

3. The kit of claim 1, wherein said dye is selected from the group consisting of 1,1'-(4,4,7,7-tetramethyl-4,7-diazaundecamethylene)-bis-4-[3-methyl-2,3-dihydro-(benzo-1,3-oxazole)-2-methylidene]-quinolinumtetraiodide (Yoyo-1), 1,1'-(4,4,7,7-tetramethyl- 4,7-diazaundecamethylene)-bis-4-[3-methyl-2,3-dihydro-(benzo-1,3-thiazole)-2-methylidene]-quinolinumtetraiodide (Toto-1) and 1,1'-(4,4,7,7-tetramethyl-4,7-diazaundecamethylene)-bis-4-[3-methyl-2,3-dihydro-(benzo-1,3-thiazole)-2-propenylidene]-quinolinum tetraiodide (Toto-3).

4. The kit of claim 1, wherein said nuclease is DNase.

5. The kit of claim 1, wherein said nuclease is RNase.

6. The kit of claim 1, wherein said nuclease acts upon a substrate selected from the group consisting of single stranded DNA, single stranded RNA, double stranded DNA, double stranded RNA, circular single stranded DNA, circular single stranded RNA, circular double stranded DNA, circular double stranded RNA, 5'-blocked single stranded DNA, 5'-blocked single stranded RNA, 5'-blocked double stranded DNA, 5'-blocked double stranded RNA, 3'-blocked single stranded DNA, 3'-blocked single stranded RNA, 3'-blocked double stranded DNA, 3'-blocked double stranded RNA, synthetic oligonucleotides with or without chemical modifications and combinations of any of the foregoing.

7. The kit of claim 1, wherein said nuclease acts upon a substrate selected from the group consisting of a mixture of two or more of single stranded DNA, single stranded RNA, double stranded DNA, double stranded RNA, circular single stranded DNA, circular single stranded RNA, circular double stranded DNA, circular double stranded RNA, 5'-blocked single stranded DNA, 5'-blocked single stranded RNA, 5'-blocked double stranded DNA, 5'-blocked double stranded RNA, 3'-blocked single stranded DNA, 3'-blocked single stranded RNA, 3'-blocked double stranded DNA, 3'-blocked double stranded RNA, synthetic oligonucleotides with or without chemical modifications and combinations of any of the foregoing.

8. The kit of claim 1, wherein said polynucleotide is selected from the group consisting of single stranded DNA, single stranded RNA, double stranded DNA, double stranded RNA, circular single stranded DNA, circular single stranded RNA, circular double stranded DNA, circular double stranded RNA, 5'-blocked single stranded DNA, 5'-blocked single stranded RNA, 5'-blocked double stranded DNA, 5'-blocked double stranded RNA, 3'-blocked single stranded DNA, 3'-blocked single stranded RNA, 3'-blocked double stranded DNA, 3'-blocked double stranded RNA, synthetic oligonucleotides with or without chemical modifications and combinations of any of the foregoing.

9. The kit of claim 1, wherein said polynucleotide is selected from the group consisting of a mixture of two or more of single, stranded DNA, single stranded RNA, double stranded DNA, double stranded RNA, circular single stranded DNA, circular single stranded RNA, circular double stranded DNA, circular double stranded RNA, 5'-blocked single stranded DNA, 5'-blocked single stranded RNA, 5'-blocked double stranded DNA, 5'-blocked double stranded RNA, 3'-blocked single stranded DNA, 3'-blocked single stranded RNA, 3'-blocked double stranded DNA, 3'-blocked double stranded RNA, synthetic oligonucleotides with or without chemical modifications and combinations of any of the foregoing.

10. A kit as in claim 1, wherein said container is attached to at least one of said control wells, wherein said nuclease in said container is isolated from the polynucleotide and dye in said control well by a perforatable separation.

11. A method for detection and quantification of nuclease activity in a test sample having an unknown quantity of nuclease activity comprising:

a. providing a plate having a plurality of wells therein, at least one of said wells being a control well and at least one of said wells being a test well, each of said test and control wells containing a known quantity of a polynucleotide and a thiazolium or azolium dye having a partition coefficient greater than $10^7$ with said polynucleotide, whereby polynucleotide-dye complexes are formed from said dye and said polynucleotide;

b. adding a known quantity of nuclease to at least one control well;

c. adding a test sample with an unknown nuclease activity to at least one test well;

d. incubating the nuclease in the control and test wells with said polynucleotide-dye complexes which are simultaneously present in said control and test wells, whereby digestion of said polynucleotide-dye complexes by nuclease occurs; and e. detecting fluorescence in the control and test wells; and f. comparing the detected amount of fluorescence from the at least one test well to the detected amount of fluorescence from the at least one control well, wherein the detected amount of fluorescence in the at least one test well being greater than the detected amount of fluorescence in the at least one control well indicates less nuclease activity in the at least one test well than in the at least one control well, and wherein the detected amount of fluorescence in the at least one test well being less than the detected amount of fluorescence in the at least one control well indicates greater nuclease activity in the at least one test well than in the control well.

12. The method as in claim 11, wherein said polynucleotide and dye are dried onto said plate.

13. The method as in claim 12, further comprising resuspending said dried polynucleotide and dye prior to adding nuclease.

14. The method as in claim 11, wherein the known quantity of nuclease added to the at least one control well is no nuclease.

15. The method as in claim 11, wherein the known quantity of nuclease added to one of said control wells is different than the quantity of nuclease added to another of said control wells.

16. A method as in claim 11, wherein the step of detecting fluorescence comprises:

i) exciting the dye in each test and control well with an appropriate wavelength of energy;

ii) measuring light energy emitted by the dye.

17. A method as in claim 11, wherein said dye is selected from the group consisting of 1,1'-(4,4,7,7-tetramethyl-4,7-diazaundecamethylene)-bis-4-[3-methyl-2,3-dihydro-(benzo-1,3-oxazole)-2-methylidene]-quinolinum tetraiodide (Yoyo-1), 1,1'-(4,4,7,7-tetramethyl-4,7-diazaundecamethylene)-bis-4-[3-methyl-2,3-dihydro-(benzo-1,3-thiazole)-2-methylidene]-quinolinum tetraiodide (Toto-1) and 1,1'-(4,4,7,7-tetramethyl-4,7-diazaundecamethylene)-bis-4-[3-methyl-2,3-dihydro-(benzo-1,3-thiazole)-2-propenylidene]-quinolinum tetraiodide (Toto-3).

18. A method as in claim 11, wherein said nuclease is DNase.

19. A method as in claim 11, wherein said nuclease is RNase.

20. A method as in claim 11, wherein said nuclease acts upon a substrate selected from the group consisting of single stranded DNA, single stranded RNA, double stranded DNA, double stranded RNA, circular single stranded DNA, circular single stranded RNA, circular double stranded DNA, circular double stranded RNA, 5'-blocked single stranded DNA, 5'-blocked single stranded RNA, 5'-blocked double stranded DNA, 5'-blocked double stranded RNA, 3'-blocked single stranded DNA, 3'blocked single stranded RNA, 3'-blocked double stranded DNA, 3'-blocked double stranded RNA, synthetic oligonucleotides with or without chemical modifications and combinations of any of the foregoing.

21. A method as in claim 11,, wherein said nuclease acts upon a substrate selected from the group consisting of a mixture of two or more of single stranded DNA, single stranded RNA, double stranded DNA, double stranded RNA, circular single stranded DNA, circular single stranded RNA, circular double stranded DNA, circular double stranded RNA, 5'-blocked single stranded DNA, 5'-blocked single stranded RNA, 5'-blocked double stranded DNA, 5'-blocked double stranded RNA, 3'-blocked single stranded DNA, 3'-blocked single stranded RNA, 3'-blocked double stranded DNA, 3'-blocked double stranded RNA, synthetic oligonucleotides with or without chemical modifications and combinations of any of the foregoing.

22. A method as in claim 11, wherein said polynucleotide is selected from the group consisting of single stranded DNA, single stranded RNA, double stranded DNA, double stranded RNA, circular single stranded DNA, circular single stranded RNA, circular double stranded DNA, circular double stranded RNA, 5'-blocked single stranded DNA, 5'-blocked single stranded RNA, 5'-blocked double stranded DNA, 5'-blocked double stranded RNA, 3'-blocked single stranded DNA, 3'-blocked single stranded RNA, 3'-blocked double stranded DNA, 3'-blocked double stranded RNA, synthetic oligonucleotides with or without chemical modifications and combinations of any of the foregoing.

23. A method as in claim 11, wherein said polynucleotide is selected from the group consisting of a mixture of two or more of single stranded DNA, single stranded RNA, double stranded DNA, double stranded RNA, circular single stranded DNA, circular single stranded RNA, circular double stranded DNA, circular double stranded RNA, 5'-blocked single stranded DNA, 5'-blocked single; stranded RNA, 5'-blocked double stranded DNA, 5'-blocked double stranded RNA, 3'-blocked single stranded DNA, 3'-blocked single stranded RNA, 3'-blocked double stranded DNA, 3'-blocked double stranded RNA, synthetic oligonucleotides with or without chemical modifications and combinations of any of the foregoing.

24. A method as in claim 11, wherein said nuclease and said test sample are incubated for between 10 and 120 minutes before determining said fluorescence.

* * * * *